US011939558B2

(12) United States Patent
Methner et al.

(10) Patent No.: US 11,939,558 B2
(45) Date of Patent: Mar. 26, 2024

(54) SPORT BEVERAGES AND METHODS FOR THEIR PRODUCTION

(71) Applicants: Technische Universität Berlin, Berlin (DE); Griffith University, Queensland (AU)

(72) Inventors: Frank-Jürgen Methner, Bitburg (DE); Thomas Kunz, Berlin (DE); Torsten Seewald, Berlin (DE); Ben Desbrow, Queensland (AU)

(73) Assignees: TECHNISCHE UNIVERSITÄT BERLIN, Berlin (DE); GRIFFITH UNIVERSITY, Queensland (AU)

( * ) Notice: Subject to any disclaimer, the term of this patent is extended or adjusted under 35 U.S.C. 154(b) by 0 days.

(21) Appl. No.: 15/565,834

(22) PCT Filed: Apr. 14, 2016

(86) PCT No.: PCT/EP2016/058257
§ 371 (c)(1),
(2) Date: Oct. 11, 2017

(87) PCT Pub. No.: WO2016/169835
PCT Pub. Date: Oct. 27, 2016

(65) Prior Publication Data
US 2018/0135000 A1   May 17, 2018

(30) Foreign Application Priority Data

Apr. 21, 2015  (EP) .................................. 15164475

(51) Int. Cl.
| | | |
|---|---|---|
| *C12G 3/025* | (2019.01) | |
| *A23L 2/52* | (2006.01) | |
| *C12C 5/00* | (2006.01) | |
| *C12C 7/047* | (2006.01) | |
| *C12C 11/00* | (2006.01) | |
| *C12C 11/06* | (2006.01) | |
| *C12C 11/11* | (2019.01) | |
| *C12C 12/00* | (2006.01) | |
| *C12G 3/021* | (2019.01) | |
| *C12G 3/026* | (2019.01) | |
| *C12H 1/00* | (2006.01) | |

(52) U.S. Cl.
CPC .............. *C12G 3/025* (2013.01); *A23L 2/52* (2013.01); *C12C 5/004* (2013.01); *C12C 7/047* (2013.01); *C12C 11/003* (2013.01); *C12C 11/06* (2013.01); *C12C 11/11* (2013.01); *C12C 12/006* (2013.01); *C12C 12/008* (2013.01); *C12G 3/021* (2019.02); *C12G 3/026* (2019.02); *C12H 1/00* (2013.01)

(58) Field of Classification Search
CPC ....... C12C 5/004; C12C 7/047; C12C 11/003; C12C 11/11; C12C 12/006; C12C 12/008; C12C 12/04; C12C 11/06; A23L 2/52; C12G 3/025; C12H 1/00
See application file for complete search history.

(56) References Cited

U.S. PATENT DOCUMENTS

| | | | |
|---|---|---|---|
| 5,762,991 A | 6/1998 | Dziondziak et al. | |
| 2003/0039721 A1* | 2/2003 | Shah ...................... | C12C 11/003 426/16 |
| 2003/0134007 A1 | 7/2003 | Donhowe | |
| 2003/0157218 A1 | 8/2003 | Donhowe | |
| 2004/0033292 A1* | 2/2004 | Portman ................... | A23L 2/39 426/72 |
| 2007/0003670 A1 | 1/2007 | Jendrysik et al. | |
| 2011/0195149 A1* | 8/2011 | Kreisz ..................... | C12C 5/004 426/13 |
| 2012/0302731 A1* | 11/2012 | Li ............................. | C12F 3/06 530/344 |

FOREIGN PATENT DOCUMENTS

| | | | | |
|---|---|---|---|---|
| ES | 2316284 A1 | 4/2009 | | |
| JP | 2007-6888 A | 1/2007 | | |
| WO | 2007113292 A2 | 10/2007 | | |
| WO | 2010084018 A1 | 7/2010 | | |
| WO | 2012140075 A2 | 10/2012 | | |
| WO | WO-2014173418 A1 * | 10/2014 | ............... | A23L 2/52 |

OTHER PUBLICATIONS

Armstrong, L. E., "Hydration Assessment Techniques." Nutrition Reviews, Sep. 2014, 63 (6): abstract.
Beneo GMBH, "Introducing the next level of carbohydrate functionality." [Retrieved on Dec. 5, 2017] Retrieved from the Internet: < URL: https://www.beneo.com/Ingredients/Human_Nutrition/Functional_Carbohydrates/>.
Bühligen, F. et al., "Analysis of agingin in lager brewing yeast during serial repitching." Journal of Biotechnology, Jul. 2014, 187: 60-70.
Desbrow, B. et al., "Beer as a Sports Drink? Manipulating Beer's Ingredients to Replace Lost Fluid." International Journal of Sport Nutrition and Exercise Metabolism, 2013, 23: 593-600.

(Continued)

*Primary Examiner* — Vera Stulii
(74) *Attorney, Agent, or Firm* — SALIWANCHIK, LLOYD & EISENSCHENK (57) ABSTRACT

The present invention relates to a method for producing a sport beverage, comprising the steps of providing malt and/or unmalted grains, providing mashing liquor produced from spent grains, processing the malt and the mashing liquor to obtain a wort, fermenting the wort by using a yeast and optionally, blending with flavour(s) and/or vitamin(s); and/or adding of sugar(s). The present invention further relates to a sport beverage obtained by said method, wherein said sport beverage is non-alcoholic or has an alcohol content of less than about 1.2 vol-%, preferably less than about 0.5 vol-%. The present invention also relates to the use of the sport beverage before and/or after physical activities.

12 Claims, 8 Drawing Sheets

(56) References Cited

OTHER PUBLICATIONS

Desbrow, B. et al., "Manipulations to the Alcohol and Sodium Content of Beer for Postexercise Rehydration." International Journal of Sport Nutrition & Exercise Metabolism, Jun. 2015, 25 (3): abstract.

Irwin, C. et al., "Alcohol pharmacokinetics and risk-taking behaviour following exercise-induced dehydration." Pharmacology Biochemistry and Behavior, Jun. 2012, 101 (4): abstract.

Kunz, T. et al., "Impact of Fermentable and Non-Fermentable Carbohydrates on the Sweetness, Improvement of Palate Fullness and SO2-Content in Beer." BrewingScience, Nov./Dec. 2012, 65: abstract.

Marsh-Richard, D. M. et al., "Adaptive Visual Scales (AVAS): A Modifiable Software Program for the Creation, Administration, and Scoring of Visual Analog Scales." Behav. Res. Methods., Feb. 2009, 41 (1): 99-106.

Phillips, S. M., "Dietary protein requirements and adaptive advantages in athletes." British Journal of Nutrition, Aug. 2012, 108 (S2): S158-S167.

Roberts, S. et al., "Glycemic response to carbohydrate and the effects of exercise and protein." Nutrition, 2013, 29: 881-885.

Scherr, J. et al., "Non-alcoholic Beer Reduces Inflammation and the Incidence of Upper Respiratory Tract Infections After a Marathon." Medicine & Science in Sports & Exercise, Jun. 2011, Board#5. DOI:http://dx.doi.org/10.1249/01.MSS.0000402720.41923.7b.

Mussatto, S.I. et al., "Brewer's spent grain: a valuable feedstock for industrial applications" J Sci Food Agric, 2013, pp. 1264-1275, vol. 94.

Office Action dated Dec. 12, 2019 by the Japanese Patent Office in the parallel Japanese Patent Application No. 2017-555689.

Office Action dated Jul. 27, 2021 by the Japanese Patent Office in the parallel Japanese Patent Application No. 2017-555689 with English translation.

\* cited by examiner

SPORT BEVERAGES AND METHODS FOR THEIR PRODUCTION

CROSS REFERENCE TO A RELATED APPLICATION

This application is a National Stage Application of International Application Number PCT/EP2016/058257, filed Apr. 14, 2016; which claims priority to European Patent Application No. 15164475.4, filed Apr. 21, 2015.

The present invention relates to a method for producing a sport beverage, comprising the steps of providing malt and/or unmalted grains, providing mashing liquor produced from spent grains, processing the malt and the mashing liquor to obtain a wort, fermenting the wort by using a yeast and optionally, blending with flavour(s) and/or vitamin(s); and/or adding of sugar(s). The present invention further relates to a sport beverage obtained by said method, wherein said sport beverage is non-alcoholic or has an alcohol content of less than about 1.2 vol-%, preferably less than about 0.5 vol-%. The present invention also relates to the use of the sport beverage before and/or after physical activities.

BACKGROUND OF THE INVENTION

The market of non-alcoholic beverages has changed in the last years because of alterations in the people's habits of consumption. On the basis of the newest medical findings the health consciousness of the people developed further and thereby new trends arose especially in the enhanced consumption of organic, eco-, prebiotic and probiotic food. The new consumer awareness also leads to a greater demand for products with health enhancing qualities. Athletes or physically active people increasingly request special sport beverages. Such sport beverages shall supply them with nutrients on a natural basis. Considering medical findings, malt extract or beer wort are adapted for the production of health enhancing beverages because of their high content of energy-rich carbohydrates, polyphenols, essential amino acids, vitamins and minerals. Furthermore the natural features of wort are suitable for growth and fermentation of many microorganisms, for instance, yeast.

Since very recently the biotechnological fermentation through other microorganisms, whose biochemical products could have a positive effect on the human metabolic pathways, aroused more interest. Therefore it is reasonable to use lactic acid bacteria to ferment wort, because the positive effects of lactic acid bacteria are most widely known and the associated products are completely accepted. However, the utilization of lactobacilli for wort fermentation is damageable towards antimicrobial agents, for example hops. Their sophisticated nutritional needs should be completely covered by the wort.

There is a need in the art for improved non-alcoholic beverages, in particular sport beverages, and methods for producing them.

SUMMARY OF THE INVENTION

According to the present invention this object is solved by a method for producing a sport beverage having an alcohol content of less than about 1.2 vol-%, preferably less than 0.5 vol-%, comprising the following steps:
(i) providing malt and/or unmalted grains;
(ii) providing mashing liquor produced from spent grains;
(iii) processing the malt and the mashing liquor to obtain a wort;
(iv) fermenting the wort by using a yeast, preferably maltose-negative yeast;
(v) optionally, blending with flavour(s) and/or vitamin(s); and
(vi) optionally, adding of sugar(s).

According to the present invention this object is solved by a sport beverage, obtained or produced by a method according to the present invention.

According to the present invention this object is solved by using the sport beverage of the present invention before and/or after physical or sports activities.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Method of Producing Sport Beverages

As discussed above, the present invention provides a method for producing a sport beverage.

Said method comprises the following steps:
(i) providing malt and/or unmalted grains;
(ii) providing mashing liquor produced from spent grains;
(iii) processing the malt and the mashing liquor to obtain a wort;
(iv) fermenting the wort by using a yeast, preferably maltose-negative yeast;
(v) optionally, blending with flavour(s) and/or vitamin(s); and
(vi) optionally, adding of sugar(s).

The sport beverage obtained by the method of the invention is preferably "non-alcoholic".

The term "'non-alcoholic" refers to a beverage, such as a sport beverage, which has an alcohol content of less than about 1.2 vol-% (according to Australian standard), preferably less than 0.5 vol-% (according to European standard).

(i) Malt and/or Unmalted Grains

In step (i) of the method of the present invention, malt and/or unmalted grains are provided.

The malt provided in step (i) of the method of the present invention preferably comprises or contains or consists of:
(a) malt
preferably 100%, or
(b) malt and barley (together 100%)
such as malt about 50 to about 100%,
barley about 0 to about 50%, In one embodiment, the malt optionally, comprises or contains in addition to (a) or (b) special malt
such as colour malt, flavour malt, munich malt, melanoidine malt,
about 0 to about 100%,
and/or
roasted malt and/or roasted barley,
such as about 0 to about 20%,
wherein, preferably, (a)+(c)=100% or (b)+(c)=100%.

In step (i), in one embodiment malt and unmalted grains are provided.

The unmalted grains are preferably barley, wheat, rye, corn or combinations thereof, more preferably barley.

The sport beverage which is obtained by the method of the present invention is based on un- or low hopped wort from malt (100%) or malt and barley with different proportions.

Additionally, for creating changes in colour and flavour special, roasted or colour malts could be admitted to the grist. A preferred recipe is shown in Table 1.

TABLE 1

Raw materials (sport beverage).

| Raw materials | [kg/30 kg grist] | [%] | Roller gap of the mill [mm] |
|---|---|---|---|
| Pilsner malt (barley malt) | 30-15 | 100-50 | 1.7 or optionally |
| Barley | 15-0 | 50-0 | 1.0 (recommended: steeping previously for 5-10 min $T_{H2O}$ = 20° C.) |
| Special malt (Colour malt) e.g. munich malt, melanoidine malt etc. | 30-0 | 100-0 | 1.7 or optionally |
| Roasted malt/roasted barley | 6-0 | 20-0 | |

Beside the recipe, the defined preparation of spent grains, malt and barley provides the basis for a good working lautering process and is the requirement for the production, the special taste and the protein content of the sport beverage obtained with the method of the present invention.

The special preparation process for the malt-barley matrix of wort also belongs to these requirements. The barley is steeped in water (temperature about 20° C.) for about 5-10 min before milling to achieve a specified size of the husk, which should facilitate the lautering process. This also serves to minimize or avoid the additional application of enzymes by processing unmalted grains.

(ii) Mashing Liquor Produced from Spent Grains

The inventors developed technological procedures and recipes to extract specific ingredients, especially the necessary proteins, which can be dissolved out of spent grains.

The term "spent grains" as used herein refers to a secondary product from wort production, in particular the insoluble components of the mash after lautering.

The spent grains are preferably barley, wheat, rye, corn or combinations thereof, preferably barley.

The technical procedures and recipes of the present invention are based on a previous patent application of the inventors for the production of non-alcoholic beverages or beers [5]. In contrast to the procedure described in the earlier patent application, an essential step for preparing the sports drink according to the present invention is the production of mashing liquor from spent grains. The proteins contained in the spent grains are preferably solubilized through mechanical crushing and the addition of technical enzymes during different rests of the mashing procedure. The high-protein mashing liquor is used directly for the production of the protein-rich sports drink of the present invention.

Preferably, the mashing liquor produced from the spent grains and provided in step (ii) is a high-protein mashing liquor.

The term "high-protein mashing liquor" or "mashing liquor with high protein content" as used herein refers to a protein content of about 10 to about 30 g/L.

In a preferred embodiment, the production of the mashing liquor preferably comprises extracting and/or solubilizing proteins contained in the spent grains.

The extraction and/or solubilizing of proteins contained in the spent grains comprises preferably the following steps:

(a) mechanical crushing of the spent grains,
(b) mixing of the mechanically broken down spent grains with brewing liquor preferably in a ratio of 1:1 to 1:1.5 (spent grains [kg]: water [L]),
(c) enzymatic degradation.

The enzymatic degradation can be carried out by thermal treatment, preferably comprising several rests.

For example, the thermal treatment can comprise:

(1) a first rest,
    e.g. at about 45° C., for about 60 min,
(2) a second rest,
    e.g. after heating up to about 75° C., for about 30 min, at about 75° C. for about 60 min
(3) optionally further rest(s),
    e.g. at about 66° C. and/or between about 5° C. to about 30° C.,
(4) optionally, a cooling down,
    e.g. to about 20 to about 30° C., or to about 5° C.

In a preferred embodiment, during step (c) technical enzymes are added, such as during the rest(s) in thermal treatment.

Said technical enzymes are preferably at least one of the following a protease,
    e.g. added during the first rest (1),
    e.g. in a concentration of about 1 to 5 g/kg spent grains,
    e.g. added at about 45° C.;
a glucanase and/or xylanase,
    e.g. added during the first rest (1) and/or second rest (2),
    e.g. in a concentration of about 0.05 to 0.3 g/kg spent grains,
    e.g. added at about 45° C. to about 75° C.;
a pullulanase (glucosidase),
    e.g. added during the first rest (1) and/or second rest (2),
    e.g. in a concentration of about 0.01 to 1 g/kg spent grains,
    e.g. added at about 45° C. to about 75° C.;
an endoprotease
    e.g. added during or after cooling at 5° C. (4),
    e.g. in a concentration of about 2 to 10 g/hL mashing liquor,
    e.g. at about 5° C. for about 8 to 12 h.

Suitable examples for technical enzymes are for a protease: Neutrase® (Novozymes); for a glucanase and/or xylanase: Ultraflo® MAX(Novozymes, enzyme mixture of glucanase and xylanase); for a pullulanase (glucosidase), Promozyme® BrewQ (Novozymes); an endoprotease: a proline-specific endoprotease, such as EC 3.4.21.26 enzyme Brewers Clarex™™ (DSM).

(iii) Processing of the Malt and the Mashing Liquor to Obtain a Wort

In an embodiment, step (iii) comprises mashing with grist and the produced mashing liquor.

In an embodiment, the mashing is carried out by or comprises thermal treatment, wherein said thermal treatment preferably comprising several rests.

For example,
(1) a first rest,
   e.g. at about 45° C., for about 20 min,
(2) a second rest,
   e.g. after heating up to about 66° C., for about 20 min,
   e.g. at about 66° C. for about 20 min
(3) a third rest,
   e.g. after heating up to about 75° C., for about 10 min,
   e.g. at about 75° C. for about 20 min,
   e.g. followed e.g. by another heating up to about 78° C., for about 3 min.

In an embodiment, step (iii) comprises lautering and boiling of the wort.

Preferably, the boiling of the wort is for about 50 min, or up to about 60 min or longer, e.g. at about 100° C.

Preferably, the boiling of the wort is with a small hop dosage or without a hop dosage, preferably a hop dosage of about 0 to 10 about IBUs.

A "small hop dosage" as used herein refers to a hop dosage corresponding to a bitterness of about 0 to about 20 international bitter units (IBUs), preferably about 5 to about 10 IBUs.

Preferably, after boiling the wort is cooled down, preferably to about 10° C.

(iv) Fermentation

For the fermentation, different yeast strains can be applied to achieve various flavours of the beverage.

In a preferred embodiment, maltose-negative yeast strains are used.

Preferably, the maltose-negative yeast for the fermentation in step (iv) is selected from
   yeast of *Saccharomycodes* sp., preferably *Saccharomycodes ludwigii*.

Maltose-negative yeast strains of preferably yeast of *Saccharomycodes ludwigii*, preferably *Saccharomycodes* sp. TK 67 (DSM accession number: DSM 24943) and *Saccharomycodes* sp. TK 77 (DSM accession number: DSM 24944), are used preferably, owing to a low production of alcohol and a high production of organic acids and fruit esters.

*Saccharomycodes* sp. TK 67 used herein refers to *Saccharomycodes* sp. TK 67 with DSM accession number: DSM 24943.

*Saccharomycodes* sp. TK 77 used herein refers to *Saccharomycodes* sp. TK 77 with DSM accession number: DSM 24944.

Through a cold-contact method or stopped fermentation at an alcohol content under 0.5 vol-% also the yeast strains *Saccharomyces cerevisiae* Saflager S-23 (available from Fermentis Division of S.I. Lesaffre, France, see e.g. www-.fermentis.com/wp-content/uploads/2012/02/SFG_S23.pdf) or *Saccharomyces pastorianus* HEBRU [2] are applicable.

Owing to the formation of less alcohol and optimised taste the yeast strains *Saccharomycodes ludwigii*, specifically *Saccharomycodes* sp. TK 67 and *Saccharomycodes* sp. TK 77, are preferred.

In a preferred embodiment, step (iii) comprises an acidification of the wort and/or adjustment of the pH.

In an embodiment, fermented wort is added, preferably during wort boiling, wherein said fermented wort was obtained in a separate/parallel fermentation step (iv)' with lactic acid bacteria,
   preferably *Lactobacillus plantarum* 210 (DSM accession number: DSM 24945) and *Lactobacillus plantarum* B1 (DSM accession number: DSM 24946).

*Lactobacillus plantarum* 210 used herein refers to *Lactobacillus plantarum* 210 with DSM accession number: DSM 24945.

*Lactobacillus plantarum* B1 used herein refers to *Lactobacillus plantarum* B1 with DSM accession number: DSM 24946.

In another embodiment, the acidification comprises addition of (synthetic) L+ lactic acid(s), preferably during wort boiling, or before or after fermentation.

For example, for the standard recipe about 0.13 mL lactic acids/100 mL beverage are added. The addition of lactic acid is preferably adjusted in a range of about 0.06 to about 0.16 mL lactic acid/100 mL beverage, taking into account the later aroma blending (e.g. blending with lemon flavour leads to a reduction of lactic acid addition).

(v) Blending with Flavour(s) and/or Vitamin(s)

In an embodiment, the blending of step (v) is carried out:
   before, during or after filtration, or
   before bottling and pasteurization, The flavour(s) are preferably selected lemon, apple, pomegranate, ginger, pineapple, elder, raspberry, rhubarb, strawberry, maracuja or combinations thereof.

The vitamin(s) are preferably selected from ascorbic acid, vitamin E, vitamin B complex (such as B, B12 complex), vitamin D or combinations thereof.

The skilled artisan can select further flavour(s) and/or vitamins.

(vi) Adding of Sugar(s)

In one embodiment, the adding of sugar(s) of step (vi) is carried out:
   at the end of the whirlpool rest (after wort boiling), or
   before cooling and fermentation, The sugar(s) are preferably selected from non-fermentable sugar(s),
   such as
   isomaltulose (added, such as, up to 6%, preferably about 2 to about 4%),
   trehalulose,
   polydextrose,
   maltodextrin,
   or combinations.

Isomaltulose is available as Palatinose™ (BENEO-Palatinit GmbH, Mannheim, Germany). Vitalose® (Biolife-Development GmbH, Wedemark, Germany) contains primarily 80% trehalulose.

The terms "non-fermentable" carbohydrates or sugars and "functional" carbohydrates or sugars are used interchangeably herein, wherein "non-fermentable" carbohydrates/sugars refer to carbohydrates/sugars that are not fermented by yeast metabolism and wherein "functional" carbohydrates or sugars refer to carbohydrates/sugars that have an inherent physiological functionality in addition to their more common nutritional value.

In one embodiment, non-fermentable carbohydrates are utilized. The resultant carbohydrate profile of the sport beverage obtained enables a continuous energy supply over several hours and qualifies the sports drink for consumption before or during sportive activities.

Further Method Steps and/or Additions

In one embodiment, the method of the present invention comprises controlling the content of NaCl.

Optionally, the addition of NaCl is comprised, preferably to a final content of at least about 25 mmol/L.

In one embodiment, the method of the present invention comprises furthermore
   filtration (such as with candle filters),
   carbonation (such as for several days),
   bottling and pasteurizing.

In one embodiment, further protein(s) in addition to the protein(s) extracted and/or solubilized from the spent grains, as described herein, are added, such as soy protein, wheat protein, milk protein or protein(s) from other natural plant sources, such as rye, oats, beans, peas, *quinoa*, amaranth.

The method of production according to the present invention results in a sport beverage with an optimal ratio of the described nutrients which is naturally achieved (range of carbohydrates, proteins, amino acids, polyphenols, vitamins, minerals (salts)). The optimal ratio of the described nutrients in the sport beverage was considered to nutritionally aspects and the biological availability respectively to an optimized endogenous uptake. The findings of researches at the School of Allied Health Sciences, Griffith University [3, 12] served as reference for the ideal composition of the ingredients in the sport beverage, which is suitable for regeneration after sportive activities.

Target Constituents
NaCl:

After sportive activities optimal regeneration and liquid intake is guaranteed through contents of NaCl between 20-50 mmol/L. A content of approx. 20 or 25 mmol/L is recommended because this concentration of sodium facilitates a physiological response (i.e. fluid retention) whilst maintaining palatability [3].

Carbohydrates:

Carbohydrates have a special importance for the regeneration of the glycogen store of the muscles after sportive activities. Additionally the content of carbohydrates affects the athlete's liquid intake. The sport beverage should have a content of carbohydrates of about 45 g/L to about 60 g/L (4.5%-6%).

Proteins:

Physiological investigations showed, that a protein intake of 20 g (whey protein) immediately afterwards of sportive activities leads to optimal stimulation of the muscle synthesis over several hours [7]. Furthermore rehydration and glycemic reaction are improved after carbohydrates intake in combination with enhanced protein contents in beverages [8]. Related to the matrix of beer a preferably high content of proteins in a range of 5 g per 750-1000 mL to about 25 g per 750-1000 mL is aspired, such as 20 g per 750-1000 mL.

The present invention allows producing amber-coloured, fizzy and non-alcoholic sports drinks, which are relevant for the different moments of sportive activities. These natural, pleasant fruity and sweetish beverage bases, which can be biologically produced as well, can be mixed and flavoured to produce a range of colour and taste varieties.

Sport Beverages and their Uses

As discussed above, the present invention provides a sport beverage, obtained or produced by a method according to the present invention.

The sport beverage of the present invention is preferably characterized by at least one of the following:
  an alcohol content of less than about 1.2 vol-%, preferably less than 0.5 vol-%,
  a NaCl content of at least about 20 mmol/L;
  a protein content of about 5.5 g per 0.75 to 1 L to about 25 g per 0.75 to 1 L;
  a carbohydrate content of about 45 g/L to about 60 g/L (about 4.5% to 6%); optionally, containing non-fermentable sugar(s), such as isomaltuose and/or trehalulose, also possible are polydextrose, maltodextrin or combinations of the sugars;
  optionally, containing flavour(s) and/or vitamin(s) such as ascorbic acid (e.g. up to 80 mg/L, preferably about 20 to 25 mg/L);

In one embodiment, the sport beverage contains non-fermentable carbohydrate(s)/sugar(s) and/or functional carbohydrate(s)/sugar(s). The resultant carbohydrate profile of the sport beverage enables a continuous energy supply over several hours and qualifies the sports drink for consumption before or during sportive activities.

As discussed above, the flavour(s) are preferably selected lemon, apple, pomegranate, ginger, pineapple, elder, raspberry, rhubarb, strawberry, maracuja or combinations thereof.

As discussed above, the vitamin(s) are preferably selected from ascorbic acid, vitamin E, vitamin B complex (such as B, B12 complex), vitamin D or combinations thereof.

The skilled artisan can select further flavour(s) and/or vitamins.

In one embodiment and as discussed above, the sport beverage contains the protein(s) extracted and/or solubilized from the spent grains as well as further proteins which can be added during the preparation, such as soy protein, wheat protein, milk protein or protein(s) from other natural plant sources, such as rye, oats, beans, peas, *quinoa*, amaranth.

As discussed above, the present invention provides the use of the sport beverage of the present invention before and/or after physical or sports activity/activities.

When the sport beverage of the present invention is used after physical or sports activity it is suitable for the body's regeneration, because it serves in/causes:
  replenishing the carbohydrates reserves of the body,
  supplying the body with necessary proteins, polyphenols, essential amino acids, vitamins and/or minerals.

The sport beverage of the present invention can be used by adults, but also children and juveniles.

The invention provides a non-alcoholic, pre- and probiotic, protein-rich, fermented sport beverage on the basis of un- or low hopped malt-barley wort. It is a novel sports drink, which could be consumed drink before, during or for the fast regeneration of the body after sportive activities. For the physical regeneration the replenishment of the carbohydrates reserves and the supply with necessary proteins, polyphenols, essential amino acids, vitamins and minerals is very important. The uptake of nutrients is accelerated through a specific solute content of the beverage.

As discussed above, by obtaining the sports beverage of the present invention with the method of production according to the present invention an optimal ratio of the described nutrients is naturally achieved (range of carbohydrates, proteins, amino acids, polyphenols, vitamins, minerals (salts)). The optimal ratio of the described nutrients in the sport beverage was considered to nutritionally aspects and the biological availability respectively to an optimized endogenous uptake. The findings of researches at the School of Allied Health Sciences, Griffith University [3, 12] served as reference for the ideal composition of the ingredients in the sport beverage, which is suitable for regeneration after sportive activities.

FURTHER DESCRIPTION OF PREFERRED EMBODIMENTS

In summary, the present invention provides:

The technical procedures and recipes of the present invention are based on a previous patent application of the inventors for the production of non-alcoholic beverages or beers [5]. In contrast to the procedure described in the earlier patent application, an essential step for preparing the sports drink according to the present invention is the production of mashing liquor from spent grains. The proteins contained in the spent grains are preferably solubilized through mechanical crushing and the addition of technical enzymes during different rests of the mashing procedure. The high-protein mashing liquor is used directly for the production of the protein-rich sports drink of the present invention.

The wort can be produced with different malts (e.g. colour and roasted malt), which were especially prepared previously, and possibly unmalted grains (barley) and afterwards fermented with various yeast strains for different tastes.

Another simultaneous fermentation with lactic acid bacteria, specifically *Lactobacillus plantarum* 210 and *Lactobacillus plantarum* B1, takes place. These lactic acid bacteria are used to acidify the wort during wort boiling. The fermentation is intentionally terminated according to defined production parameters and it follows the maturation process. In a simplified method the malt-barley wort is fermented only with yeast and the lactic acid is not produced by lactic acid fermentation, but rather it is added as synthetic L+ lactic acid during wort boiling, before or after fermentation.

The next process step, principally before filtration, is a blending with flavours (e.g. lemon, apple, pomegranate, ginger, pineapple, etc.) and vitamins (e.g. ascorbic acid). The mixing is also possible after filtration or before bottling and pasteurization. The beverage (without additional flavour) or the flavoured beverages are filtered with candle filters and afterwards carbonated for several days. After sufficient carbonation the beverage is bottled and pasteurized.

The produced sports drink contents <0.5 Vol. % alcohol and therefore it can be declared as alcohol-free. It has a high content of energy-rich carbohydrates, proteins, polyphenols, essential amino acids, vitamins and minerals. Because of its balanced composition of nutrients it is well tolerable. The most important vitamins of the B-complex, further biotin, and also precious proteins and vital minerals like magnesium, calcium, phosphor and potassium are available in the sports drink and therefore it is not only suitable for adults, but also for the growing organism of children and juveniles. The enhanced content of polyphenols operates anticarcinogenic, antioxidative, anti-inflammatory, blood pressure and blood glucose regulating [6].

Another option is the addition of functional sugars like isomaltulose, Vitalose® to the sport beverage (for standard procedure up to 6% (2-4%), also a higher addition is possible). Thereby a better palatefulness and a balanced carbohydrate intake over an extended period are guaranteed. Glucose is quickly integrated into the metabolism, whereas isomaltulose (Palatinose™) or Vitalose® (primarily 80% trehalulose) lead to a retarded carbohydrate supply of the body. In summary the combination of the naturally available carbohydrates of the wort (glucose, fructose, sucrose, maltose, maltotriose, other oligosaccharides, dextrins) and the addition of functional carbohydrates like isomaltulose (Palatinose™) and/or Vitalose® lead to a balanced supply with carbohydrates before or during sportive activities (see FIG. 1).

Figure 1:
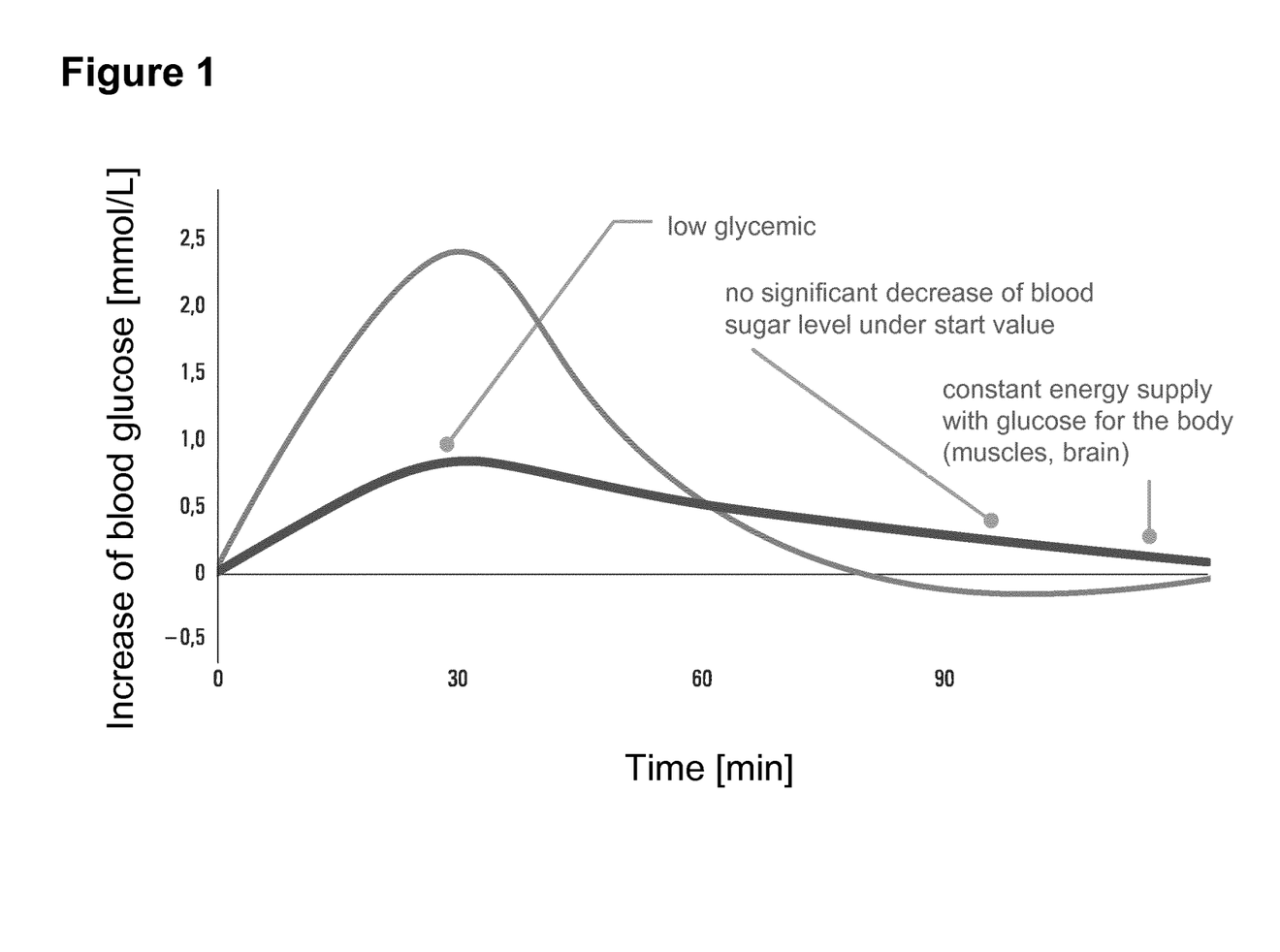
FIG. 1: Increase of blood glucose during the uptake of sucrose (grey) (similar to glucose) compared with isomaltulose (blue) [1].

The different uptake of carbohydrates is represented in FIG. 1 using the example of the increase of blood glucose through the uptake of sucrose and isomaltulose (Palatinose™). This comparison shows clearly the consistent and extended energy supply through the uptake of isomaltulose (Palatinose™). It has to be pointed out, that by analogy of saccharose the additionally contained fructose, glucose or maltose are quickly absorbed as well and they are well suited for the body's carbohydrates supply. By analogy of isomaltulose (Palatinose™) the functional carbohydrate trehalulose (Vitalose®) shows a consistent and extended carbohydrate supply and is thereby very suitable to support the carbohydrate intake during a prolonged sportive activity.

In further detail, the present invention provides:

The sport beverage of the present invention is based on un- or low hopped wort from malt (100%) or malt and barley with different proportions. Additionally, for creating changes in colour and flavour special, roasted or colour malts could be admitted to the grist. The recipe is shown in Table 1, see above.

Beside the recipe, the defined preparation of spent grains, malt and barley provides the basis for a good working lautering process and is the developmentally requirement for the production, the special taste and the protein content of the sport beverage.

To these developmentally requirements belongs the special preparation process for the malt-barley matrix of wort. The barley is steeped in water (temperature 20° C.) for 5-10 min before milling to achieve a specified size of the husk, which should facilitate the lautering process. This also serves to minimize or avoid the additional application of enzymes by processing unmalted grains.

Figure 2:
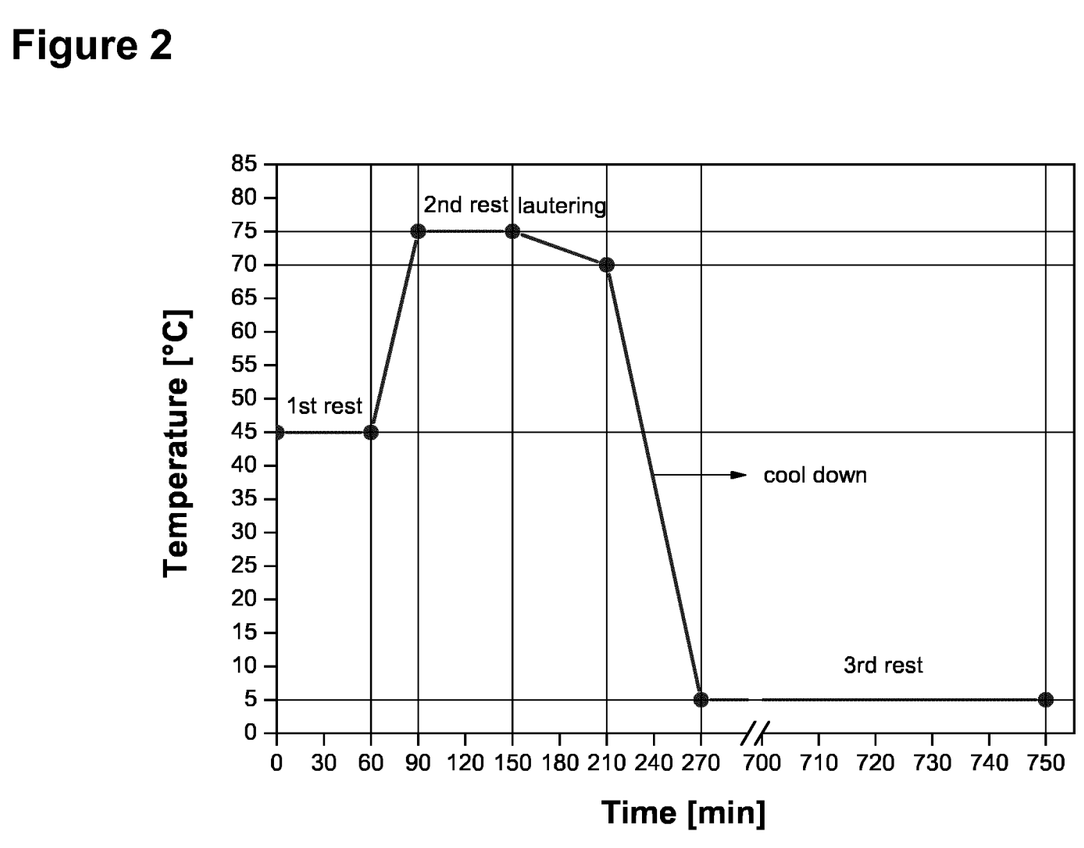
FIG. 2: Example of a preferred thermal treatment for the enzymatic degradation of spent grains and the preparation of the mashing liquor for the production of a sport beverage.

Especially the extraction of proteins from spent grains for the preparation of mashing liquor belongs to the developmentally requirements. For this process remained spent grains are treated mechanically and enzymatically to produce mashing liquor with a high protein content. The first step of preparation is the mechanical crushing of the spent grains. For this purpose a meat grinder (e.g. hole diameter of 3-5 mm) is useful. However, the mechanical preparation is also possible with other equipment. The mechanically broken down spent grains are mixed with brewing liquor in a ratio of 1:1 to 1:1.5 (spent grains [kg]:water [L]). Afterwards the thermal treatment for enzymatic degradation, shown in FIG. 2, is mainly used to dissolve a maximum of proteins. The presented thermal treatment is just one possibility of enzymatic degradation of spent grains. Each rest could be varied in holding time and an additionally rest e.g. at 66° C. or later on between 5-30° C. is possible as well to increase the yield. The cooling down to <5° C. mainly enables the storage of the mashing liquor. If the produced mashing liquor is used immediately afterwards the cooling down to <5° C. is not necessary (cooling down to 20-30° C. is sufficient). Even a faster or slower cooling after lautering is another possibility.

Addition of Enzymes (Mashing Liquor):

The enzymatic degradation of the spent grains is supported by different technical enzymes. During the first rest a protease can be added (e.g. Neutrase®, company Novozymes, in a concentration of 1-5 g/kg spent grains). The addition is made during manufacturing process at 45° C. or at the beginning of mashing-in of the spent grains. Afterwards a glucanase and/or xylanase can be added and for another alternative pullulanase (glucosidase) can be used (e.g. Ultraflo® MAX, company Novozymes, enzyme mixture of glucanase and xylanase, in a concentration of 0.05-0.3 g/kg spent grains, added at 45-75° C. (FIG. 2, 1st and 2nd rest) and possibly for another alternative pullulanase (glucosidase) e.g. Promozyme® BrewQ, company Novozymes, in a concentration of 0.01-1 g/kg spent grains added at 45-75° C. (FIG. 2, 1st and 2nd rest)). The following addition of enzymes takes place during or after cooling at 5° C. with an endoprotease (e.g. enzyme Brewers Clarex™™ from the company DSM) in a concentration of 2-10 g/hL mashing liquor. The 3rd enzyme treatment proceeds at approx. 5° C. for 8-12 h (FIG. 2, 3rd rest).

Figure 3:
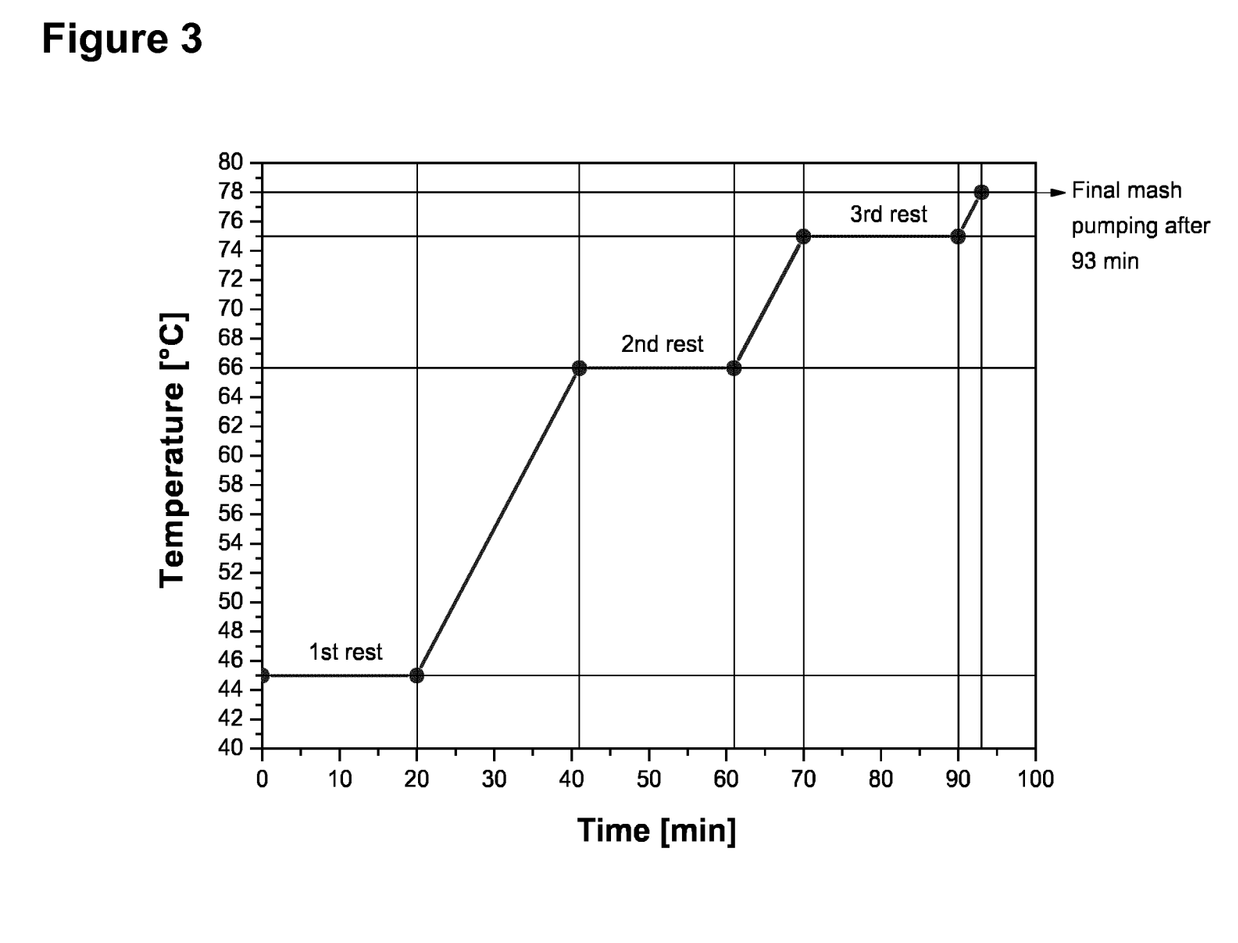
FIG. 3: Example of the mashing procedure to produce a sport beverage using the prior produced protein-rich mashing liquor.

Mashing Procedure:

As an example, the mashing procedure as shown in FIG. 3 is applied with appropriate grist (Table 1) and the produced mashing liquor. The presented mashing procedure is a preferred option. The rests and their holding times can be varied and additional rest can be applied to increase the yield.

Lautering and Boiling:

Lautering ends with "kettle-full". Afterwards the wort is boiled at 100° C. for 60 min (a boiling time of 50 min is preferred, also longer boiling times than 60 min to adjust the extract are possible, but it leads to a lower flavour stability) with a small or without a hop dosage. The extract is adjusted to 6-12% GV depending on the desired sweetness and palatefulness. For the standard method for producing a sport beverage the extract was set between 6.5 and 8.0%.

For the additional alternative with applying functional sugars (e.g. isomaltulose (Palatinose™), Vitalose® (80% trehalulose)) the extract is adjusted between 2.0-12.0% GV. The functional carbohydrates are added at the end of the whirlpool rest or before cooling and fermentation. Thus it can be taken advantage of the positive effects of the functional carbohydrates during fermentation (e.g. $SO_2$ formation) according to the literature [2]. However, a later or earlier addition of functional carbohydrates during the manufacturing process is possible as well.

For all modifications of the sport beverage, an acidification of the wort is necessary for the desired amount of lactic acid and the adjustment of the pH value. With lactic acid bacteria specifically *Lactobacillus plantarum* 210 and *Lactobacillus plantarum* B1, fermented wort is added during boiling (preferably after 20-30 min of boiling time) to set the pH value of the original wort. A simplified method to achieve the desired pH value is the addition of synthetic L+ lactic acid(s) to the wort during boiling, before or after fermentation.

The wort remains for 10-30 min in the whirlpool and afterwards the wort is cooled down to 10° C. The fermentation is purposefully terminated according to defined production parameters and the maturation process follows.

Fermentation:

For the fermentation of the malt (100%) or malt-barley worts, different yeast strains are applied to achieve various flavours of the beverage. Maltose negative yeast strains of *Saccharomycodes ludwigii*, specifically *Saccharomycodes* sp. TK 67 and *Saccharomycodes* sp. TK 77, are used preferably, owing to a low production of alcohol and a high production of organic acids and fruit esters.

Through a cold-contact method or stopped fermentation at an alcohol content under 0.5 vol-% also the yeast strains *Saccharomyces cerevisiae* Saflager S-23 (available from Fermentis Division of S.I. Lesaffre, France, see e.g. www-.fermentis.com/wp-content/uploads/2012/02/SFG_S23.pdf) or *Saccharomyces pastorianus* HEBRU [2] are applicable.

Preferred Fermentation Conditions for Maltose-Negative Yeast Strains of *Saccharomycodes ludwigii*, *Saccharomycodes* sp. TK 67 and *Saccharomycodes* sp. TK 77:
Extract original wort: 6.0-9.0% GV or 6.8-8.0% GV
Time of fermentation: 40-120 h or 48-96 h
Temperature of fermentation: 10-26° C. or 16-22° C.
Amount of pitching yeast cells: $0.5 \times 10^6$ C/mL $5 \times 10^6$ C/mL When functional carbohydrates (e.g. isomaltulose (Palatinose™), Vitalose®, etc.) were used, the extract content is respectively elevated. The fermentation is terminated after a degradation of extract about 0.7-0.8% GV with a pH value of 4.0-4.6.

Conditions of the Separate Lactic Acid Fermentation:
Lactobacilli: strains of lactic acid bacteria, *Lactobacillus plantarum* 210 and *Lactobacillus plantarum* B1:
Time of fermentation: 48-120 h or approx. 72 h
Temperature of fermentation: 22-32° C. or 26-28° C.
Amount of pitching yeast cells: $0.5 \times 10^6$ C/mL $10 \times 10^6$ C/mL or
$1 \times 10^6$ C/mL $6 \times 10^6$ C/mL The fermentation ends when the pH value reaches the range of pH 3.1-3.4.

For the standard recipe 0.13 mL lactic acids/100 mL beverage are added. Basically the addition of lactic acid has to be adjusted in a range of 0.06-0.16 mL lactic acid/100 mL beverage taking into account the later aroma blending (e.g. blending with lemon flavour leads to a reduction of lactic acid addition).

After analytical control the content of NaCl possibly has to be adjusted through adding NaCl. Target value min. 25 mmol/L.

The beverage (without additional flavour) or the flavoured beverages are filtered with candle filters and afterwards carbonated for several days. After sufficient carbonation the beverage is bottled and pasteurized. The produced sport beverage contents <0.5 Vol. % alcohol and therefore it can be declared as alcohol-free.

Blending:

After finishing fermentation it follows the maturation. The next process step, principally before filtration, is a blending with flavours (lemon, peach, apple, pomegranate, ginger, pineapple, etc.) and vitamins (e.g. ascorbic acid up to 80 mg/L→standard recipe concentration of ascorbic acid 20-25 mg/L). The blending is also possible after filtration or before bottling and pasteurization. Here it has to be considered, that some flavours, e.g. ginger flavour, lead to haze formation in the beverage. For those flavours blending prior filtration is advantageous.

Carbonation, Bottling, Pasteurization:

After filtration and blending the sport beverage is carbonated. After sufficient carbonation it is bottled and pasteurized until at least 25 pasteurization units.

The produced sport beverage contents <0.5 Vol. % alcohol and therefore it can be declared as alcohol-free.

The following examples and drawings illustrate the present invention without, however, limiting the same thereto.

EXAMPLES

Example 1

Experimental Trials and Comparison Between a Sport Beverage of the Present Invention and a Commercial Sport Beverage and a Commercial Mid-Strength Beer 1. Methods 1.1 Participants Eleven healthy recreational active males [29.0±6.9 y, 176±4 cm, 75.5±7.9 kg; values are mean±SD] volunteered to participate as participants in the prototype study. Participants were all non-smokers with an average reported habitual alcohol intake in the 3 months prior to the study ranging from 2.5-150 g·week$^{-1}$. All participants were fully informed of the nature and possible risks of the study before giving their written informed consent. The investigation was approved by the institutional Human Research Ethics Committee of Griffith Health Institute, Griffith University, Nathan, Queensland, Australia.

1.2 Experimental Design

Participants visited the laboratory on three occasions with their diet and exercise being standardised before each trial. Experimental trials consisted of exercise-induced weight loss (target 2.0% body mass) followed by consumption of a test beverage containing either 1) a commercial carbohydrate electrolyte beverage
   Powerade®
   0% ABV, 111 kJ·100 mL$^{-1}$, 7.0 g·100 mL$^{-1}$ CHO, 15 mmol·L$^{-1}$ Na$^+$,
2) a mid-strength beer
   XXXX Gold®
   3.5% ABV, 121 kJ·100 mL$^{-1}$, 1.9 g·100 mL$^{-1}$ CHO, 3 mmol·L$^{-1}$ Na$^+$ (subject to slight seasonal variation), or
3) a prototype beer (i.e. a sport beverage according to the invention)
   Prototype
   0.5% ABV, 95 kJ·100 mL$^{-1}$, 4.6 g·100 mL$^{-1}$ CHO, 5.3 g·L$^{-1}$ Protein, 22 mmol·L$^{-1}$ Na$^+$.

Total drink volumes in each trial were equivalent to 150% of body mass loss during exercise, consumed over a 1 h period. The order of beverage treatment was randomised using an incomplete latin square design. Measures of net fluid balance, urine production, breath alcohol concentration, plasma osmolality, haemorheology and subjective ratings of gastrointestinal tolerance were collected as dependent variables across a subsequent 4 h rest period.

1.3 Exercise and Dietary Standardisation

Experimental trials were separated by at least 7 d and were conducted at the same time of the day in a stable laboratory environment (19±2° C., ~55% relative humidity). Participants were instructed to refrain from consuming alcohol for 48 h and caffeine-containing substances for 12 h before each experiment. Participants were also asked to refrain from heavy exercise 24 h prior to each trial and any light exercise was to be completed by 1200 h the day before the experimental trials. Finally, participants were encouraged to drink fluid throughout the day but instructed to cease food and fluid consumption from 2100 h on the evening prior to trials. Food and exercise diaries were used to record their diet/exercise habits prior to the first trial and then to encourage repetition of these behaviours prior to subsequent trials. On arrival at the laboratory (0600 h) subjects verbally confirmed compliance to pre-trial diet and exercise procedures and undertook a breath alcohol compliance check (Alcolizer Technologies Inc, Brisbane, Australia) and a urine specific gravity ($U_{SG}$) measure. In the event of a $U_{SG}$ recording >1.02 subjects were asked to consume a small amount of water (range 500-1000 mL) until a $U_{SG} \leq 1.02$ could be established. On confirmation of a standard breakfast consisting of fruit bread, jam and apple juice was then supplied which provided approximately 30 kJ·kg$^{-1}$ body mass of energy, 1 g·kg$^{-1}$ body mass of carbohydrate, 3.2 mg·kg$^{-1}$ body mass of sodium and 125 mL of fluid. The breakfast was designed to provide participants with some food for the subsequent 5-6 h testing period whilst minimising fluid and sodium intakes.

1.4 Experimental Protocol

Following breakfast a 30 min rest period was taken before the participants were instructed to empty their bladder as completely as possible and a nude body mass was measured using a calibrated electronic scale to the nearest 10 g (AND Mercury DX6000). Participants then commenced exercise dressed in warm clothes designed to increase the heat and subsequent sweat losses while cycling. Exercise intensity was initially set at 60% of the subject's peak power output aiming to produce a 2% reduction in the subject's body mass. For their first trial subject's cycled for 45 min before dismounting, drying with a towel and taking a nude body mass. From this point the exercise intensity was self-selected. Subsequent nude body mass measurements were taken at regular intervals until 1.8% of the subject's initial body mass was lost, at which point the subject stopped cycling to allow the remainder of mass loss to occur throughout the cool down. During all subsequent trials participants exercised using the same intensities established within the first trial for 10 min less than the total exercise time before the first nude body mass was collected. If 1.8% body mass deficit was not achieved participants were instructed to continue exercising until this goal was reached. A rest period of 30 min occurred after the exercise phase to allow participants to have a cool shower, return to a cool environment and rest. On completion of this period a final nude body mass was taken to determine the volume of fluid required for consumption during the rehydration phase.

Over the next 60 min, the subjects ingested one of the rehydration beverages. The entire beverage volume, equal to 150% of the change in body mass, was divided into four equal parts, each of which was consumed over a 15 min period. All beverages aliquots were served cold (~4° C.), immediately from the same refrigerator. For the subsequent 4 h observation period, participants remained within the laboratory, and were seated except for essential movements.

1.5 Test Beverage Preparation

Powerade® (ready to drink) and XXXX Gold® commercial beverages were purchased at the same time, to minimise the influence of additional and/or different ingredients throughout production.

The Prototype beverage was manufactured by Technische Universitat Berlin and is a sport beverage according to the present invention with the following characteristics:
   0.5% ABV (i.e. alcohol content),
   95 kJ·100 mL$^{-1}$,
   4.6 g·100 mL$^{-1}$ CHO (i.e. carbohydrate content),
   5.3 g·L$^{-1}$ Protein,
   22 mmol L$^{-1}$ Na$^+$ 1.6 Subjective Measures (Results not Provided)

Questionnaires were conducted during the rehydration phase of the study to examine palatability of the different beverages and gastrointestinal (GI) symptoms. The palatability questionnaire was administered with the second and last of the four beverages aliquots and consisted of ratings of overall pleasantness, saltiness, sweetness and bitterness. The GI questionnaire was conducted prior to the first beverage (baseline), at 15 min following the second and the last drink and at hourly intervals until the end of the observation period. Participants were asked to rate feelings of thirst, fullness, hunger, energy, tiredness, alertness and dryness of mouth. All measures were conducted on a 100 mm visual analogue scale (VAS) ranging from "not at all" to "a lot" administered using a laptop computer [9].

1.7 Fluid Balance and Breath Alcohol Measures

Total urine loss was calculated from the total accumulated urine output in the period from the commencement of drinking until the end of the observation period (i.e. 5 h total). Participants were permitted to urinate as required throughout the observation period, with urine collected into pre-weighed containers. Hourly urine output was calculated following requested voiding at the conclusion of each hour throughout this 5 h period. Net fluid balance was calculated by subtracting the body mass (post voiding) from the initial body mass. When used across an acute time period, it is proposed that this non-invasive parameter will take into account urinary losses, sweat loss and other insensible losses and arrive at the value of complete hydration status [10].

Breath alcohol concentrations (BrAC) were analysed using a police grade Alcolizer LE breathalyser (Alcolizer Pty Ltd., Brisbane, QLD, Australia), which had been recently calibrated by the manufacturer. All breathalyser measurements were taken in duplicate, with a triplicate measure recorded if readings differed by ≥0.005%. The measures were averaged to provide the final assessment of BrAC. Previous research from our laboratory has indicated the inter-trial coefficient of variation for the breathalyser is 2.5% [11]. Participants were not informed of their BrAC measures until after completion of the entire study. As described, an initial breath alcohol sample was taken to confirm participants reported to the laboratory having completed a period of alcohol abstinence. The second breath alcohol sample occurred 15 min after completing the rehydration phase. This short period was used to avoid contamination from alcohol that may have remained within the mouth. Further breath samples were collected at 1, 2, 3 and 4 h throughout the observation period. Results are expressed as a percentage.

1.8 Blood Measures (Haemorheology Methods Excluded)

Blood samples for the determination of plasma osmolality were collected via venipuncture immediately before exercise, immediately after exercise, and then at 1 h and 4 h of the observation period. Blood samples were immediately decanted into EDTA tubes prior to centrifugation (Sigma 3K10) at 3000 rpm for 10 minutes at 4° C. The resultant plasma was then extracted for the determination of osmolality (Osmomat 030, Gonotec GmbH, Germany).

1.9 Statistical Analysis

All statistical procedures were performed using SPSS for Windows, Version 22 (SPSS Inc., Chicago, IL). One way repeated measures ANOVA was used to determine any variation between trial on initial body weight, percentage body mass change, exercise time and total urine volume. Two way (treatment and time) repeated measures ANOVA was used to compare hourly urinary volume, net fluid balance, plasma osmolality and subjective questionnaire ratings. Post hoc analysis (LSD) was performed on all significant F ratios. Significant differences were accepted when P≤0.05. All data are reported as mean±SD.

2. Results 2.1 Standardisation Procedures and Exercise Induced Dehydration

All participants arrived at the laboratory and reported compliance with the pre-trial dietary and exercise control conditions. Participants began each trial without detectable breath alcohol. Participant's initial body mass prior to exercise was similar between trials (Powerade=75.6±8.0 kg, Prototype=75.6±8.0 kg, Mid=75.3±8.1 kg, all p>0.05). Participants were successful in achieving similar relative levels of hypohydration after the exercise protocol in each of the three conditions (Powerade=2.12±0.1%, Prototype=2.06±0.2%, Mid=2.11±0.3%, all p>0.05). Additionally, the mean exercise time required to induce the dehydration did not differ between trials (Powerade=69±8 min, Prototype=64±14 min, Mid=63±13, all p>0.05).

2.2 Beverage and Alcohol Consumption

Volumes of beverages consumed varied between participants according to their initial bodyweight and degree of hypohydration. The mean volume of beverage consumed was not different between trials (Powerade=2.40±0.32 l, Prototype=2.34±0.32 l, Mid=2.39±0.43 l, all p>0.05). This equated to an alcohol intake of ~10 g (Prototype), ~65 g (Mid) on trials involving beer consumption. On ten occasions (5 prototype and 5 Mid trials) participants were unable to consume the required beverage volume within the allocated (1 hr) drinking period. To avoid emesis participants were encouraged to slow the rate of drinking of the final beverage aliquot. Despite this, no statistical differences were observed in drinking rates between trials (Powerade=60±0 min, Prototype=67±11 min, Mid=66±9 min, all p>0.05).

2.3 Urine Volume and Fluid Balance

Figure 4:
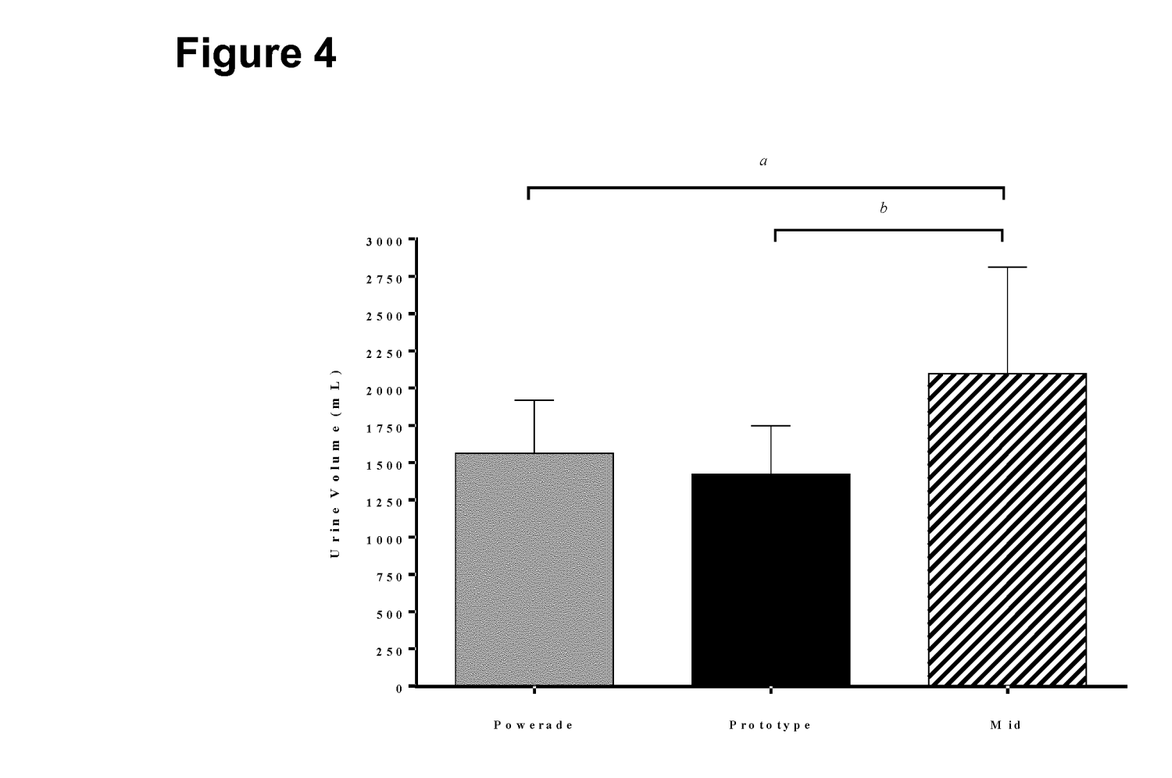
FIG. 4: The total urine volumes following the 4 hr observation period in the trials of Example 1.
Figure 5:
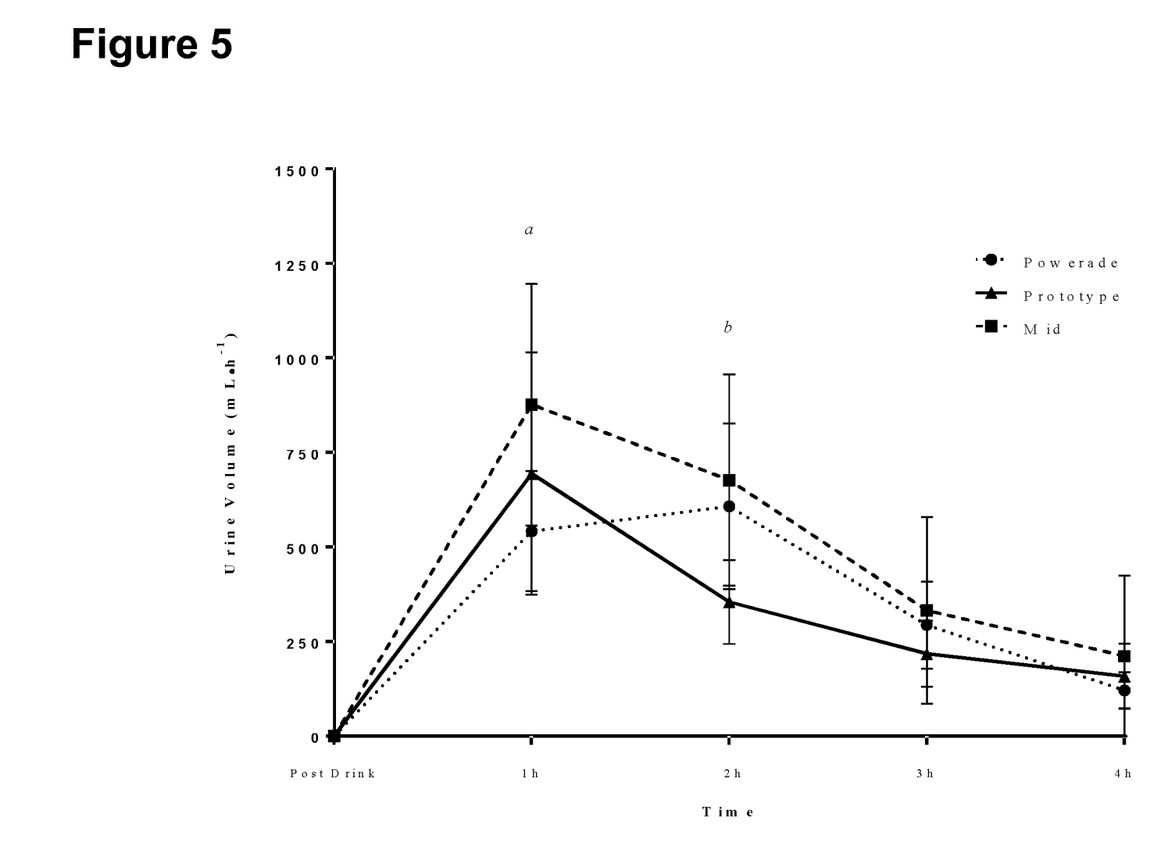
FIG. 5: Volumes of urine produced per hour throughout the 4 hr observation period in the trials of Example 1.

The total urine volumes for each trial are shown in FIG. 4 and the volumes of urine produced per hour for each trial are shown in FIG. 5. A significant main effect for treatment, $F(2,20)=7.51$; $p=0.004$, time, $F(3,30)=31.87$; $p<0.001$, and time x treatment interaction, $F(6,60)=5.12$; p $p<0.001$ was observed for hourly urine production. Significantly larger hourly urine volumes were observed on the Prototype and Mid trials compared to the Powerade trial during the first hour of the observation period (Powerade=542±159 ml, Prototype=695±321 ml, Mid=877±320 ml, Powerade-Prototype p=0.04, Powerade-Mid p<0.01). Over the next hour the urine production on the Prototype trial reduced and was significantly lower than the other trials (Powerade=608±219 ml, Prototype=355±111 ml, Mid=677±280 ml, Powerade-Prototype p<0.01, Prototype-Mid p<0.01). No further differences in hourly urine production between trials were evident.

Figure 6:
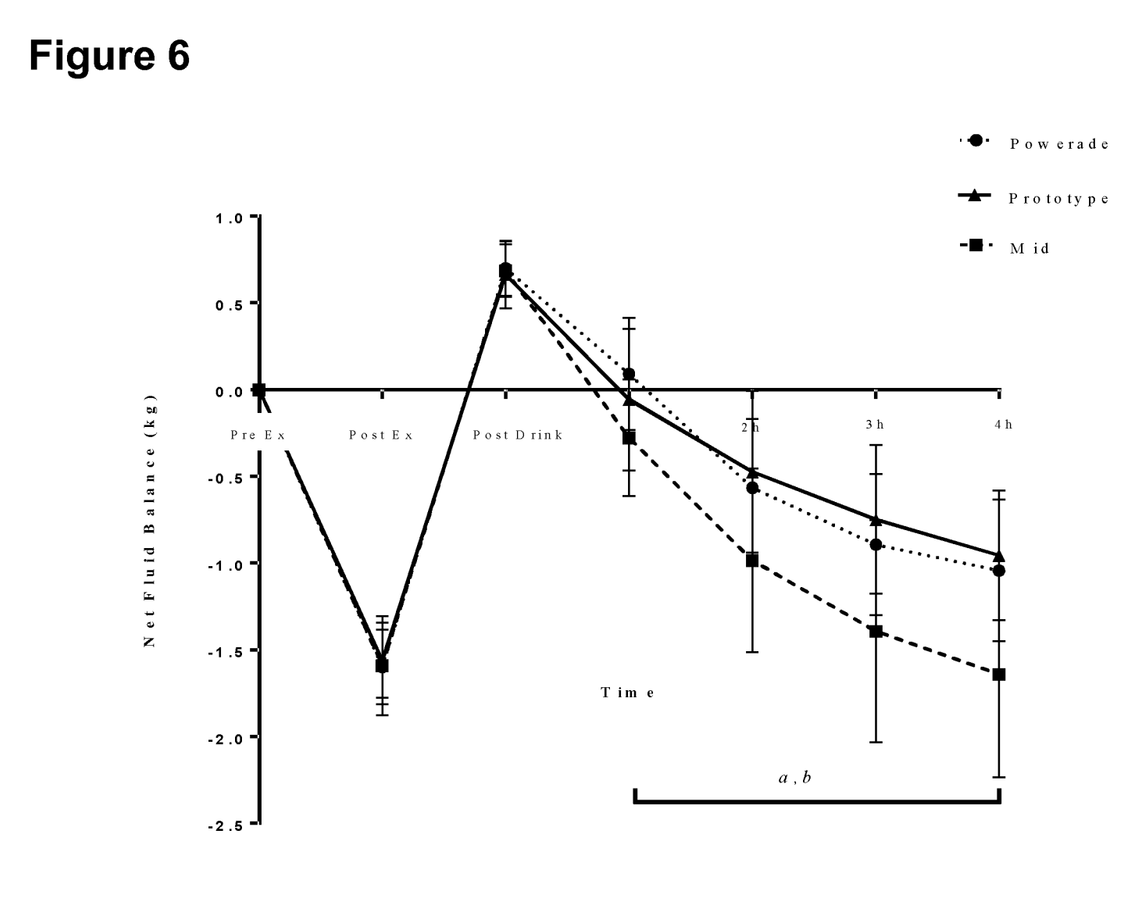
FIG. 6: Net body mass balance calculated by change in body mass throughout the 4 hr observation period in the trials of Example 1.

Net body mass balance values for each trial are shown in FIG. 6. All experimental treatments concluded with participants in a state of negative fluid balance relative to pre-exercise values (Powerade=−1.04±0.45 kg, Prototype=−0.95±0.37 kg, and Mid=−1.64±0.59 kg). A significant main effect for treatment, $F(2,20)=11.57$; $p<0.001$, time, $F(6,60)=125.57$; $p<0.001$, and time x treatment interaction, $F(12,120)=8.52$; $p<0.001$ was observed for net body mass balance.

Significantly improved net body mass balance occurred on the Powerade and Prototype trials compared to the Mid trial 1 h following drink consumption. This difference remained until the completion of the observation period (both Powerade-Mid and Prototype-Mid p<0.01 at end of observation period). These differences can be largely accounted for by the lower total urine outputs observed following consumption of Powerade and the Prototype beer (Powerade=1564±356 mL, Prototype=1425±324 mL, and Mid=2099±716 mL trials (Powerade-Mid p=0.02, Prototype-Mid p=0.02)). No statistical difference in net body mass balance was observed between Powerade and Prototype at any time point.

2.4 Breath Alcohol Concentrations

Figure 7:
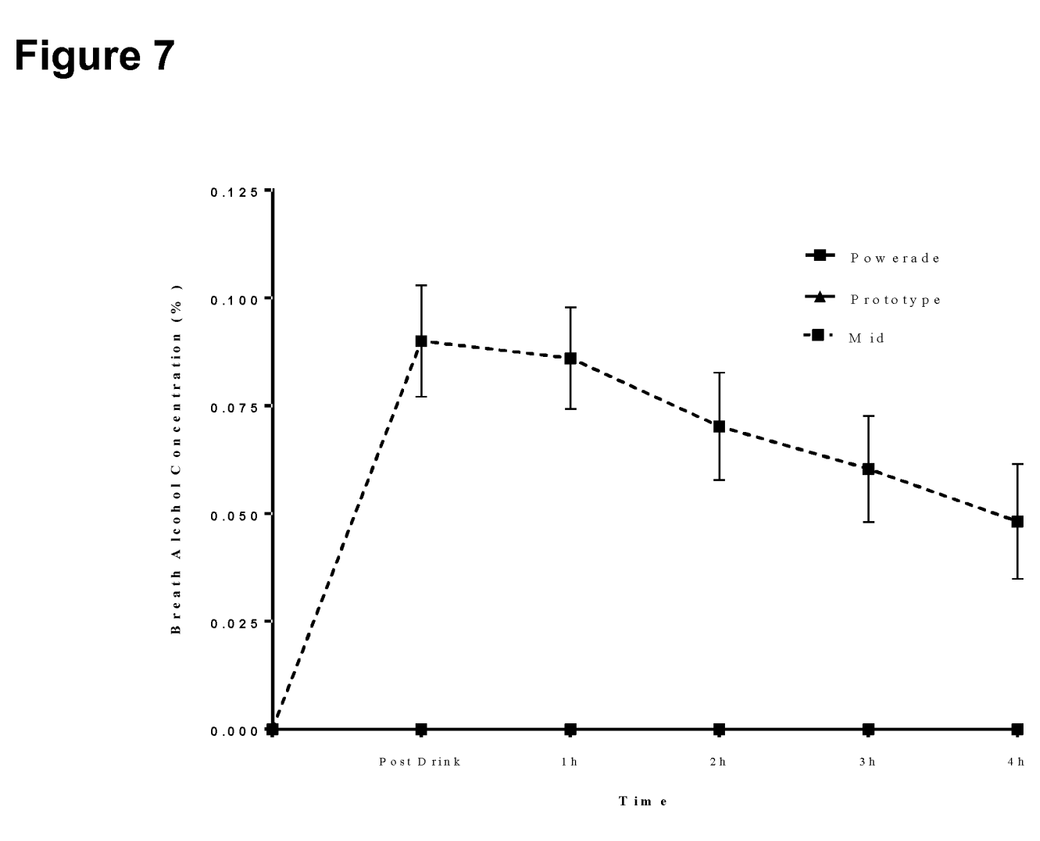
FIG. 7: Breath alcohol concentrations throughout the 4 hr observation period in the trials of Example 1.

The mean breath alcohol measures for all trials are shown in FIG. 7. No detectable breath alcohol values were recorded on the Prototype trials. Peak breath alcohol values were recorded 15 min after the cessation of drinking on the Mid trials.

2.5 Plasma Osmolality

Figure 8:
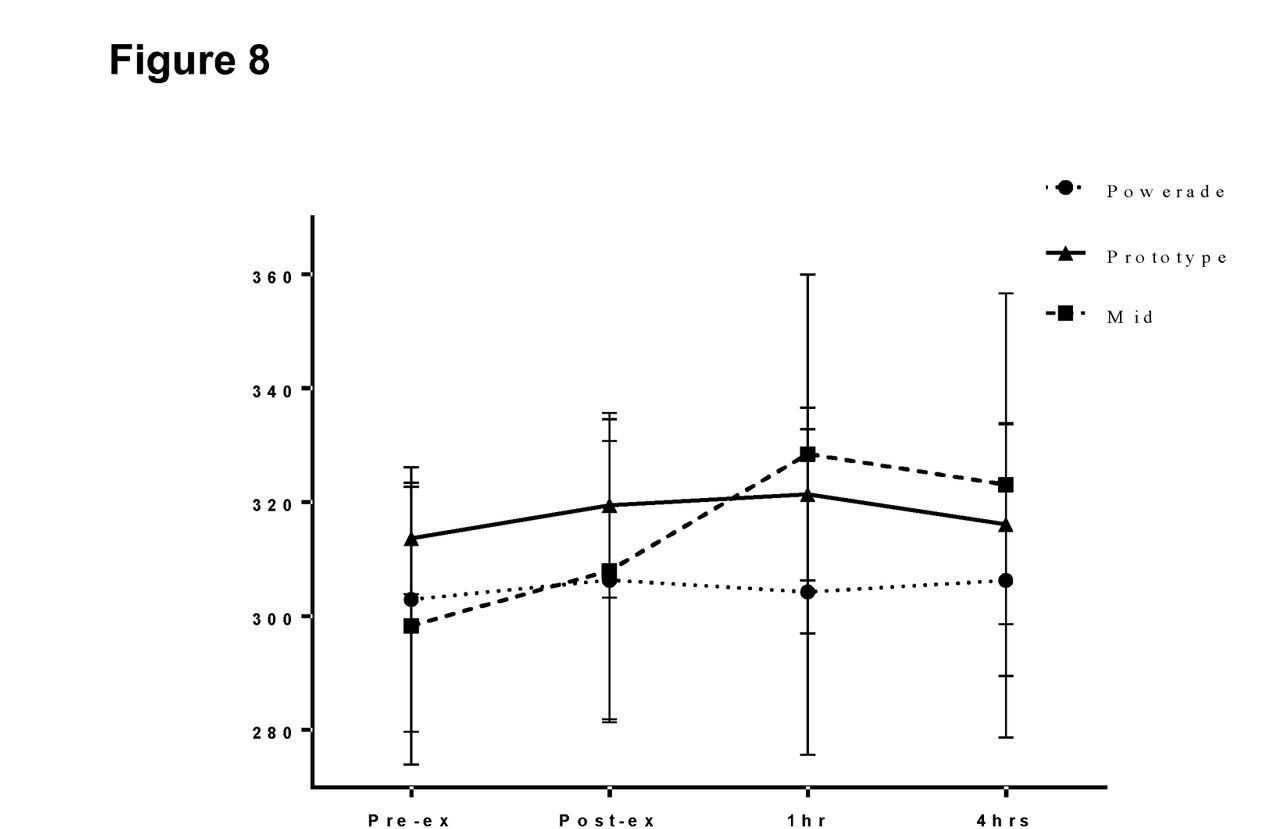
FIG. 8: Mean plasma osmolality throughout the trials of Example 1.

Measures of plasma osmolality are shown in FIG. 8. Plasma osmolality was not influenced by either time or beverage treatment.

CONCLUSION

The prototype beer used in this investigation displayed equivalent post exercise fluid restoration capacity to a commercial carbohydrate-electrolyte (sports drink) beverage. Both the prototype beverage and the sports drink where more effective at replacing exercise induced sweat losses than a mid-strength (3.5% ABV) commercial beer.

The features disclosed in the foregoing description, in the claims and/or in the accompanying drawings may, both separately and in any combination thereof, be material for realizing the invention in diverse forms thereof.

REFERENCES

[1] BENEO-Palatinit GmbH: Palatinose™—das niedrig glykämische Kohlenhydrat. (www.beneo-palatinit.com/de/Food_Ingredients/Isomaltulose/Nutritional_Benefits_of Isomaltulose/OnePager_LOW_GI_DE_2009Sep.pdf), Status as of Dec. 8, 2012.

[2] Bühligen, F., Lindner, P., Fetzer, I., Stahl, F., Scheper, T., Harms, H. and Müller, S.: Analysis of aging in lager brewing yeast during serial repitching. Journal of Biotechnology, 187, 60-70, 2014.

[3] Desbrow, B., Murray, D. and Leveritt, M.: Beer as a Sports Drink? Manipulating Beer's Ingredients to Replace Lost Fluid. International Journal of Sport Nutrition and Exercise Metabolism, 23, 593-600, 2013.

[4] Kunz, T., Reinhardt, Ch., Eon-Jeong, L., Dörr, T., Radowski, A. and Methner F.-J.: Impact of Fermentable and Non-Fermentable Carbohydrates on the Sweetness, Improvement of Palate Fullness and $SO_2$-Content in Beer. BrewingScience, Vol. 65, November/December, 2012.

[5] Methner, F.-J. and Kunz, T.: Verfahren zur Herstellung eines Getränks WO 2010/084018 A1 and DE 10 2009 005 971.7.

[6] Piendl, A.: Bier and Gesundheit, Neuere Erkenntnisse liber die Vorzüge eines maßvollen Biergenusses. Shaker Verlag, Aachen 2008, S. 83.

[7] Phillips S M. Dietary protein requirements and adaptive advantages in athletes. *The British journal of nutrition*. 2012; 108 Suppl 2:S158-167.

[8] Roberts, S., Desbrow, B., Grant, G., Anoopkumar-Dukie, S. and Leveritt, M.: Glycemic response to carbohydrate and the effects of exercise and protein. Nutrition, 29, 881-885, 2013.

[9] Marsh-Richard D M, Hatzis E S, Mathias C W, Venditti N, Dougherty D M. Adaptive Visual Analog Scales (AVAS): a modifiable software program for the creation, administration, and scoring of visual analog scales. Behav Res Methods. 2009; 41(1):99-106.

[10] Armstrong L E. Hydration assessment techniques. Nutr Rev. 2005; 63(6 Pt 2):540-54. Review.

[11] Irwin C, Goodwin A, Leveritt M, Davey A K, Desbrow B. Alcohol pharmacokinetics and risk-taking behaviour following exercise-induced dehydration. Pharmacol Biochem Behav. 2012; 101(4):609-16.

[12] Desbrow B, Cecchin D, Jones A, Grant G, Irwin C, Leveritt M. Manipulations to the Alcohol and Sodium Content of Beer for Post Exercise Rehydration. *Int J Sport Nutr Exerc Metab*. 2015.

The invention claimed is:

1. A method for producing a sport beverage having an alcohol content of less than about 1.2 vol-%, comprising the following steps:
   (i) providing malt and/or one or more unmalted grains;
   (ii) providing mashing liquor produced from spent grains, wherein said mashing liquor has a protein content of about 10 to about 30 g/L;
   (iii) processing the malt and/or one or more unmalted grains and the mashing liquor to obtain a wort;
   (iv) fermenting the wort by using a maltose-negative yeast;
   (v) blending the wort or fermented wort with one or more flavours and/or vitamins and/or adding one or more sugars to the wort or fermented wort,
   wherein the production of the mashing liquor comprises extracting and/or solubilizing proteins contained in the spent grains,
   wherein the extraction and/or solubilizing of proteins contained in the spent grains comprises:
   (a) mechanical crushing of the spent grains,
   (b) mixing the mechanically broken down spent grains with brewing liquor, and
   (c) enzymatic degradation comprising the addition of two or more technical enzymes to the mechanically broken down spent grains mixed with brewing liquor, wherein said two or more technical enzymes include at least a protease and at least one of a glucanase and/or xylanase, a pullulanase, or an endoprotease, and
   wherein the sugar(s) added in step (v) are selected from non-fermentable sugar(s).

2. The method of claim 1, wherein:
   (a) step (i) comprises providing malt without an unmalted grain, or
   (b) step (i) comprises providing malt and an unmalted grain, said unmalted grain comprising unmalted barley, and,
   (c) step (i) comprises, in addition to (a) or (b) providing one or more special malts selected from a colour malt, a flavour malt, a munich malt, a melanoidine malt, and a roasted malt and/or roasted barley.

3. The method of claim 1, wherein the one or more unmalted grains are selected from barley, wheat, rye, corn, and combinations thereof.

4. The method of claim 1, wherein the step of processing the malt and/or one or more unmalted grains and the mashing liquor to obtain a wort comprises mashing wherein the malt and/or one or more unmalted grain and the produced mashing liquor are subject to thermal treatment, wherein said thermal treatment comprises at least 3 rests as follows:
   (1) a first rest, at about 45° C., for about 20 min,
   (2) a second rest, after heating up to about 66° C., for about 20 min, at about 66° C. for about 20 min
   (3) a third rest, after heating up to about 75° C., for about 10 min, at about 75° C. for about 20 min, followed by another heating up to about 78° C., for about 3 min.

5. The method of claim 1, wherein step (iii) comprises lautering and boiling of the wort, wherein the boiling of the wort is for at least about 50 min at about 100° C., and wherein the boiling of the wort is with a hop dosage corresponding to a bitterness of about 0 to about 20 IBU in the final beverage, and wherein, after boiling, the wort is cooled down to about 10° C.

6. The method of claim 1, wherein the yeast for the fermentation in step (iv) is selected from *Saccharomycodes* sp. TK 67, *Saccharomycodes* sp. TK 77, *Saccharomyces cerevisiae* (Saflager S-23) and *Saccharomyces pastorianus* HEBRU.

7. The method of claim 5, wherein step (iii) comprises an acidification of the wort,
wherein fermented wort is added during wort boiling, and
wherein said fermented wort was obtained in a separate/parallel fermentation step (iv) with lactic acid bacteria.

8. The method of claim 1, wherein the blending of step (v) is carried out:
before bottling and pasteurization, and wherein the flavour(s) are selected from lemon, apple, pomegranate, ginger, pineapple, elder, raspberry, rhubarb, strawberry, maracuja and combinations thereof and the vitamin(s) are selected from ascorbic acid, vitamin E, vitamin B complex, vitamin D and combinations thereof.

9. The method of claim 5, wherein the adding of sugar(s) of step (v) is carried out:
after wort boiling and at the end of a whirlpool rest, or
before the wort is cooled and fermented according to step (iv).

10. The method, according to claim 1, wherein, step (b) comprises mixing the mechanically broken down spent grains with brewing liquor in a ratio of 1:1 to 1:1.5 (spent grains [kg]: water [L]).

11. The method, according to claim 1, wherein the enzymatic degradation comprises a thermal treatment comprising a first rest (1) and a second rest (2) and, optionally, a cooling down, and wherein said one or more technical enzymes include at least one of the following:
a protease, added during the first rest (1), in a concentration of about 1 to 5 g/kg spent grains, added at about 45° C.;
a glucanase and/or xylanase, added during the first rest (1) and/or second rest (2), in a concentration of about 0.05 to 0.3 g/kg spent grains, added at about 45° C. to about 75° C.;
a pullulanase, added during the first rest (1) and/or second rest (2), in a concentration of about 0.01 to 1 g/kg spent grains, added at about 45° C. to about 75° C.; and/or
an endoprotease, added during or after cooling at 5° C., in a concentration of about 2 to 10 g/hL mashing liquor, at about 5° C. for about 8 to 12 h.

12. The method, according to claim 1, wherein the non-fermentable sugar(s) are selected from trehalulose, polydextrose, maltodextrin and combinations thereof,
wherein the method further comprises adding NaCl to the sport beverage to a final content of at least about 25 mmol/L, and/or adding proteins to the sport beverage, wherein the proteins are selected from soy protein, wheat protein, milk protein and protein(s) from other plant sources; and
wherein the method further comprises: filtering the wort and/or fermented wort, before, during and/or after the blending in step (v); carbonating the sport beverage; bottling the sport beverage; and pasteurizing the sport beverage.

* * * * *